United States Patent [19]

Barchas et al.

[11] Patent Number: 5,169,852
[45] Date of Patent: Dec. 8, 1992

[54] METHOD OF SUPPRESSING APPETITE BY ADMINISTRATION OF TETRAHYDRO-BETA-CARBOLINE DERIVATIVES

[75] Inventors: Jack D. Barchas, Los Angeles; Glen R. Elliott, Sunnyvale; Peter I. Adriaenssens, Palo Alto, all of Calif.; Robert S. Bitner, West Lafayette, Ind.; Stephen S. Bowersox, Menlo Park, Laszlo Nadasdi, both of San Francisco, Calif.

[73] Assignee: Neurex Corporation, Menlo Park, Calif.

[21] Appl. No.: 628,692

[22] Filed: Dec. 14, 1990

Related U.S. Application Data

[63] Continuation-in-part of Ser. No. 363,504, Jun. 8, 1989, Pat. No. 4,978,669.

[51] Int. Cl.$^5$ .......................................... A61K 31/435
[52] U.S. Cl. ...................................... 514/292; 514/909
[58] Field of Search ............................ 514/292, 909

[56] References Cited

U.S. PATENT DOCUMENTS 4,336,260  6/1982  Payne et al. .................... 514/292
4,452,815  6/1984  Wurtman et al. ............... 514/292

FOREIGN PATENT DOCUMENTS 1183219  4/1970  United Kingdom ............... 514/292

OTHER PUBLICATIONS

Iijima et al Chemical Abstracts, vol. 105, 1986 Abstract 191049s.
Biere, Chemical Abstracts, vol. 104, 1984, Abstract 72711j.
Iijima et al Chemical Abstracts vol. 103, 1985, Abstract 160488p.
Dewar et al JACS vol. 84, 1982, pp. 3548 to 3552.
Capy and Sutherland, Advanced Organic Chemistry, 2nd Ed. (1984: Plenum Press, New York) pp. 17 to 23.
Rommelspacher et al. Chemical Abstracts vol. 87, 1977, Abstract 958936.
Huttunen, P. & Myers, R. D., Pharmacology, Biochemistry & Behavior (U.S.A.), (1986) 24:1733-1738.
Airaksinen, M. M. & Kari, I., Medicinal Biology (1981) 59:190-211.
Buckholtz, N. S., Life Sciences (1980) 27:893-903.
Rommelspacher, H., et al., Arch. Pharmacology, (1977) 298:83-91.
Verloop, A., in "Drug Design" vol. III, Chapter 2, (1972) (E. J. Ariens, ed.) Academic Press, N.Y.
Hansch, C., in "Drug Design" vol. I, Chapter 2, (1971) (E. J. Ariens, ed.) Academic Press, N.Y.

Primary Examiner—Robert T. Bond
Assistant Examiner—E. C. Ward
Attorney, Agent, or Firm—Peter J. Dehlinger; Carol A. Stratford

[57] ABSTRACT

Compounds of formula I are useful for suppressing appetite, and for altering macronutrient preferences,

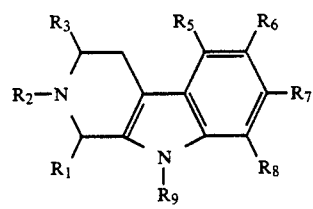

where the $R_2$-$R_9$ substituents are so selected as to meet a defined quantitative structure activity relationship (QSAR) quantity relating to the partition coefficient of the compound, the net charge on the ring nitrogen, and the radical superfdelocalizability at the position-8 ring carbon.

2 Claims, 7 Drawing Sheets

METHOD OF SUPPRESSING APPETITE BY ADMINISTRATION OF TETRAHYDRO-BETA-CARBOLINE DERIVATIVES

This application is a continuation-in-part of co-pending U.S. patent application for "Method of Suppressing Appetite by Administration of Tetrahydro-Beta-Carboline Derivatives," Ser. No. 363,504, filed Jun. 8, 1989, now U.S. Pat. No. 4,978,669.

FIELD OF THE INVENTION

This invention relates to pharmacologic control of appetite. More specifically, this invention relates to methods for suppressing feeding behavior and modifying macronutrient preference, and compounds useful therefore.

REFERENCES

Airaksinen et al, *Med Biol* 59:190-211 (1981).
Boyce, C.B.C., Milbrow, B.V., *Nature (London)*, 208, 537, (1965).
Chou, J.T., JurS, P.C., *J. Chem. Inf. Comp. Sci.*, 19(3), p. 172, (1979).
S. Cooper, *Eur J Pharmacol* 120:257-65 (1986).
Dewar, M.J.S., Grisdale, P.J., *J. Am. Chem. Soc.*, 84, p.3548, (1962).
Gallo, R. *Prog. Phys. Org, Chem.*, 14, p.115, (1983).
Glassman et al., *Science* 226:864 (1984).
Hansch, C. in *Drug Design* (E.J. Ariens, ed.), Vol. I, p. 271, Academic Press, (1971).
Hansch, C., Leo, A., *Structure-Activity Correlation*, Wiley, (1979).
P. Huttunen et al, *Pharmacol Biochem & Behav* 24:1733-38 (1986).
Jaffe, *Chem. Rev.*, 53, 191 (1953).
March, J., *Advanced Organic Chemistry* $3^{rd}$ ed., Chapter 9, Wiley (1985).
Martin, E.W., "Remington's Pharmaceutical Sciences," (Mack Pub. Co.).
Robertson, H.A., et al., *Eur J Pharmacol* 76: 281-84 (1981).
H. Rommelspacher; Airaksinen et al, *Med Biol* 59:190-211 (1981).
H. Rommelspacher et al, Naunyn-Schmiedeberq's *Arch Pharmacol* 298:83 91) (1977).
P. Skolnick et al, in "Beta-Carbolines and Tetrahydroisoquinolines" pp. 233-52, Alan R. Liss, NY (1982).
Tabachnick, B.G., Fidell, L.S., *Using Mathematical Statistics*, Chapter 5, Harper and Row (1989).
Unger, S.H., Hansch, C., *Prog. Phys. Org, Chem.*, 12, p.91 (1976).
Verloop, A et al:, in *Drug Design* (E.J. Ariens, ed.), Vol. VIII, Chapter 2, pp. 133-181, Academic Press (1976)

BACKGROUND OF THE INVENTION

The high prevalence of obesity in the United States suggests a lack of existing medical treatments. Most of the existing anorectic agents carry high risks and provide limited efficacy, precluding them as treatments of choice for the management of moderate overeating. Since there is a growing awareness in the medical community that obesity and its side-effects can require aggressive medical intervention, new anti-obesity agents with improved performance characteristics are inclined to be well received.

Although the classification and biochemical mechanisms of obesity and related eating disorders are not clearly defined, their broadening acceptance as disease states suggests a need to design safe and effective pharmacotherapies. The most commonly used weight control agents available without prescription are adrenergic stimulants such as phenylpropanolamine and phenethylamine derivatives. Although effective appetite inhibitors, adrenergic agents produce numerous untoward side effects, such as nervousness, irritability, insomnia, dizziness, tachycardia, palpitations, hypertension, and the like. These side effects may be severe enough to require cessation of treatment. The actual safety of such adrenergic agents is questionable, particularly since 20-30% of the U.S. population suffer from hypertension. Kopf, DE 3,430,389, disclosed weight reduction by administering a combination of an adrenergic agent with a benzodiazepine sedative. Although the non-stimulant anorectic agent fenfluramine is devoid of the psychomotor stimulant properties and abuse potential seen with stimulant-like compounds (e.g., amphetamine), it often has an inadequate clinical efficacy, and patients receiving the drug often complain of drowsiness and headache. Thus, it is apparent that none of the current anti-obesity pharmaco-therapies available are particularly satisfactory.

Tetrahydro-$\beta$-carboline (THBC) has a variety of pharmacological actions and has been variously evaluated as a cholinesterase inhibitor, sedative/hypnotic, analgesic, and psychotomimetic. It competes with low affinity for brain tryptamine, imipramine, 5-hydroxytryptamine (5-HT), and spiperone binding sites, enhances epolarization- induced 5 HT efflux from brain slices, and weakly inhibits 5-HT uptake in brain synaptosomes and 5-HT oxidative deamination. It occurs naturally in mammalian brain tissue.

When THBC is administered parenterally to laboratory animals, it suppresses locomotion, exploratory activity, and conflict behavior, impairs performance on operantly conditioned learning and memory tasks, reduces seizure susceptibility, prolongs barbiturate sedation, and antagonizes specific drug induced stereotypic behavior. When given in high doses, THBC induces a characteristic behavioral syndrome characterized by hyperactivity, forepaw treating, body weaving, and circling. Paradoxically, THBC has been reported to reduce motor activity, induce apparent anxiety, and increase voluntary ethanol consumption when administered intraventricularly to rats. Atkinson, GB 1,183,219 disclosed its use as an analgesic.

Physiological actions of THBC include effects on endocrine secretory patterns and body temperature. Systemic administration in rodents produces a dose-dependent elevation of plasma prolactin levels, decreased serum luteinizing hormone levels, and elevated plasma corticosterone. THBC elicits significant hypothermia when administered to rats parenterally in doses of 6.25 mg/Kg or greater.

It is also known that daily oral administration of THBC produces *temporary* dose-related decrements in food and fluid intake in rats. Animals that receive average daily amounts of THBC in excess of 49 mg/Kg show significant reductions in food intake after two consecutive days of treatment; however, tolerance develops, and food consumption returns to normal by the twelfth treatment day. Smaller daily doses (less than 30 mg/Kg) do not significantly alter appetite. It is noteworthy that in Rommel-spacher's report, 6 out of the 24 animals receiving 49 mg/Kg/day or greater died.

Payne et al, U.S. Pat. No. 4,336,260 disclosed the use of 1 aryl-3-carboxylic acid THBC derivatives as antidepressants.

S. Cooper disclosed that three fully-unsaturated β-carboline derivatives exhibit hyperphagic activity, while another β-carboline derivative exhibits anorectic activity. The hyperphagic derivatives were: ethyl 6-benzyloxy-4-meth-oxymethyl-β-carboline-3-carboxylate, ethyl-5-benzyloxy-4-methoxymethyl β-carboline-3-carboxylate, and ethyl -isopropoxy-4-methyl-β-carboline-3-carboxylate. The anorectic derivative was β-carboline-3-carboxylic acid methyl amide, which when injected intraperitoneally at 10.0 mg/Kg, reduced food consumption by partially sated rats to 30% of control.

It has been reported (Skolnick) that certain carboxy-ester beta-carboline derivatives bind with high affinity to benzodiazepine receptors. This binding may account for the ability of these compounds to antagonize the anticonvulsant, anxiolytio, and sedative properties of benzodiazepine drugs. However, saturated derivatives such as 3-carbomethoxy-1,2,3,4-tetrahydro-β-carboline bind with very low affinity (Skolnick; Robertson).

SUMMARY OF THE INVENTION

It is therefore one objective of the present invention to provide a method of appetite suppression in mammals.

It is another objective of the present invention is to provide a composition capable of selectively suppressing carbohydrate appetite in mammals.

In accordance with the invention, it has been discovered that certain derivatives of THBC, when administered in a pharmaceutically effective dose, partially or fully suppress feeding behavior. The compounds of the invention are effective at relatively low doses. These compounds are also useful for the selective alteration of macronutrient preferences (e.g., by reducing appetite for carbohydrates). The compounds of the invention exhibit very low affinity for 5-HT receptors, 5-HT uptake sites, and benzodiazepine receptors. Thus, it would appear that the compounds of the invention act by a mechanism different from that reported for saturated β-carbolines.

One aspect of the invention is the method of suppressing feeding behavior in a mammal by administering an effective amount of a compound of formula (I), where $R_2$, $R_3$, $R_5$, $R_6$, $R_7$, $R_8$ and $R_9$ are as described below:

The compounds used in the method exhibit strong structure-activity relationships. These relationships have been quantitatively analyzed to predict the properties of substituents which correlate with high appetite-suppression activity, e.g., activity substantially higher than that of THBC. The analysis relates the drug's biological activity, measured in terms of $-LogIC_{50}$ (the concentration of drug required to reduce the mammal's food intake by 50%), to the hydrophobicity of the substituents and their electronic effects on the indole portion of the molecule. Presently preferred compounds for use in suppression of appetite are those wherein $R_2$, $R_3$, $R_5$, $R_6$, $R_7$, $R_8$ and $R_9$ are selected such that the quantity $-0.0491\pi^2 + 0.416\pi + 0.118(qC_9\%) - 0.041(S'C_8R) - 2.139$, which is a measure of the predicted activity, measured in terms of LOG $(1/IC_{50})$, is between about $-1.2$ and $-1.7$ and preferably between about $-1.2$ and $-1.5$. Examples of such compounds are those in which $R_9 = n-C_5H_{11}$ and $R_2$, $R_3$, $R_6 = R_7 = R_8 = H$, and $R_9 = n-C_5H_{11}$, $R_6 = CH_3$, and $R_2 = R_3 = R_7 = R_8 = H$.

Another aspect of the invention is a Composition useful for suppression of feeding behavior in a mammal, which comprises a pharmaceutically acceptable excipient in combination with an effective amount of a compound of formula I.

Another aspect of the invention is a method for partially suppressing appetite in a mammal, by administering a compound of formula (I) where $R_2$, $R_3$, $R_6$, $R_7$, $R_8$ and $R_9$ are as described below. Another aspect of the invention is a composition for partially suppressing appetite in a mammal.

DETAILED DESCRIPTION OF THE INVENTION

Section A establishes the definitions of several terms used herein. In Section B the general synthetic methods by which the compounds of the invention may be synthesized are described. Section C provides specific descriptions of the synthetic routes to the compounds of the invention, and presents evidence of their efficacy as appetite suppressants. Section D describes the Quantitative Structure Activity Relationship (QSAR) analysis performed with the most active appetite-suppression compounds.

A. DEFINITIONS

The term "feeding behavior" as used herein refers to food intake and associated behavior. "Partial suppression" of feeding behavior refers to reduction of feeding behavior to a level between about 20% and about 70% of control behavior.

The term "effective amount" refers to the amount of a selected compound of formula I which is necessary to cause suppression of feeding behavior. The precise amount required will vary depending upon the particular compound selected, the age and weight of the subject, route of administration, and so forth, but may easily be determined by routine experimentation. Suitable experiments are described in the Examples. In general, however, an effective amount will range from about 1 mg/Kg to about 100 mg/Kg, preferably about 2 mg/Kg to about 30 mg/Kg, more preferably about 4-12 mg/Kg. Partial suppression of feeding behavior is effected by administration of similar amounts of the appropriate derivatives of formula I.

The term "appetite-altering amount" refers to the dosage of compound required to alter the appetite for carbohydrates experienced by the subject animal, i.e., to alter the subject's macronutrient preferences. The term "appetite-altering amount" also applies to the quantity required to effect a change in chemical ependency; in other words, a therapeutic amount in the treatment of e.g., alcohol, tobacco, narcotic or opiate addiction. The precise appetite-altering amount required will vary with the particular compounds employed, the species, age and condition of the subject to be treated. However, the amount may be determined by one of ordinary skill in the art with only routine experimentation, following methods known in the art, and disclosed below. In general, an appetite-altering amount will be roughly one half to one tenth the effective amount described above. Thus, the appetite altering amount will range from about 0.01 to about 10 mg/Kg body weight, preferably about 0.5-5 mg/Kg, and most preferably about 1 mg/Kg.

The term "pharmaceutically acceptable" refers to a compound, salt, or excipient which is not unacceptably toxic to the subject to which it is administered. Pharmaceutically acceptable salts include inorganic anions such as chloride, bromide, iodide, sulfate, sulfite, nitrate, nitrite, phosphate, and the like, and organic anions such as acetate, malonate, pyruvate, propionate, cinnamate, tosylate, and the like. Pharmaceutically acceptable excipients are described at length by E.W. Martin, in "Remington's Pharmaceutical Sciences."

B. GENERAL SYNTHETIC METHODS

Figure 1:
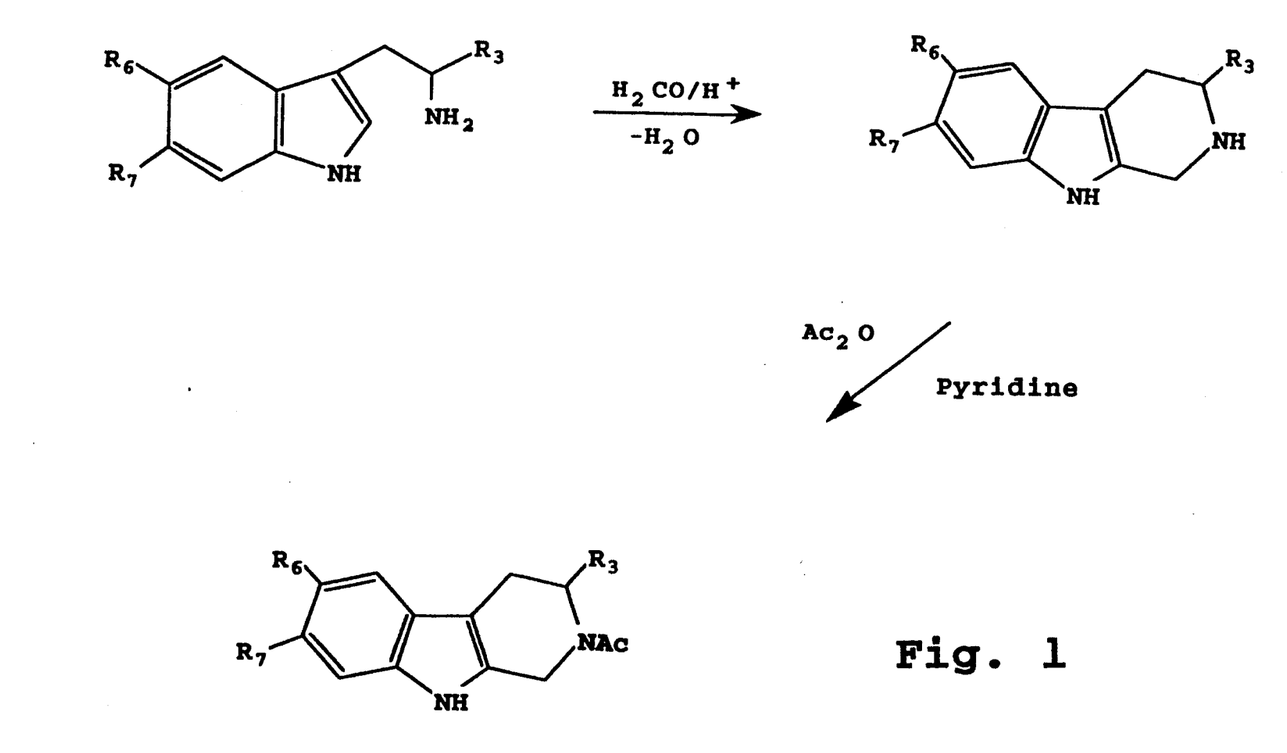
FIG. 1 illustrates one method of synthesizing substituted 1,2,3,4-tetrahydro-β-carbolines.
Figure 2:
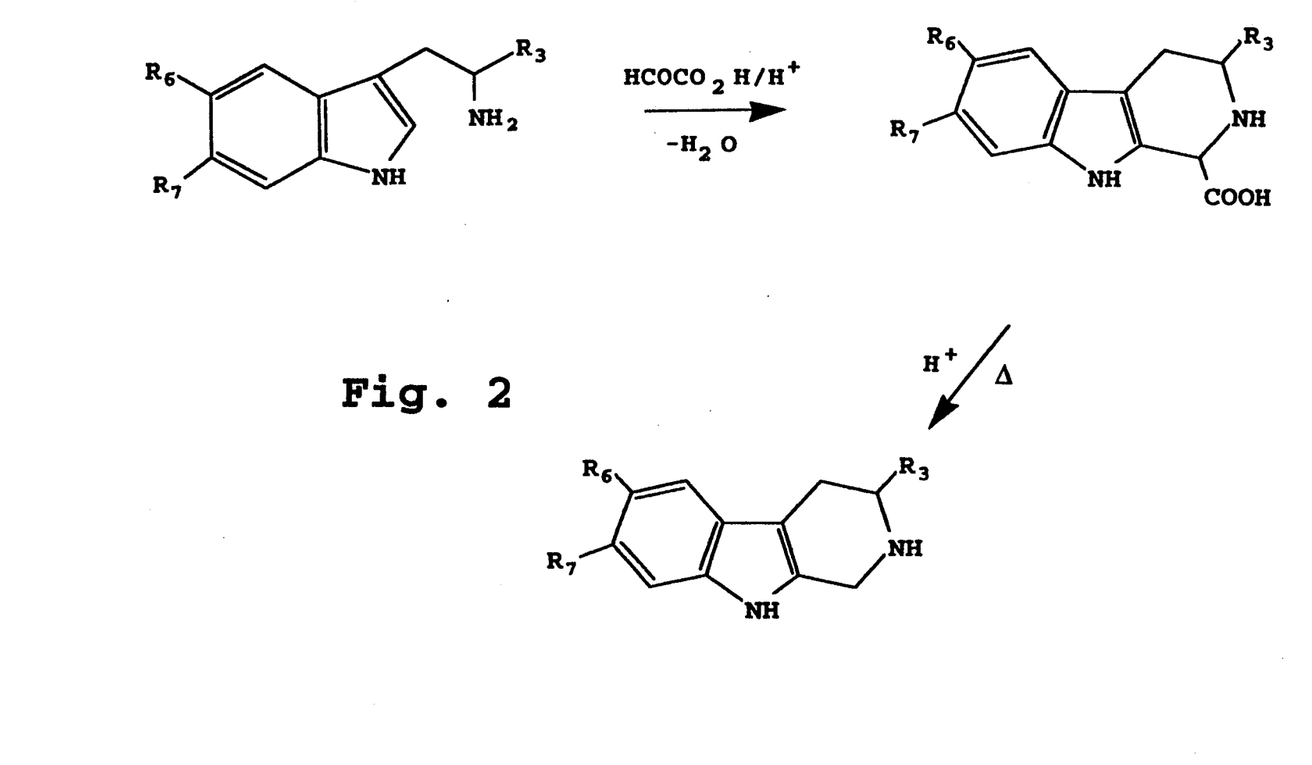
FIG. 2 illustrates a second method of synthesizing substituted 1,2,3,4-tetrahydro-β-carbolines.

Compounds of the invention may be prepared by a variety of methods known to those of ordinary skill in the art (M. Cain et al, *J Med Chem* (1982) 25:1081-91). Three exemplary methods are presented in FIGS. 1-3. FIGS. 1 and 2 illustrate two methods of forming the fused three-ring skeleton with substituents at the aromatic and aliphatic positions of the compounds, and FIG. 3 demonstrates the addition of a substituent $R_9$ at the aromatic nitrogen. Specific examples are provided in Section C below.

In FIG. 1, a substituted tryptamine is cyclized by reaction with an formaldehyde under acid catalysis to form a tetrahydro-$\beta$-carboline derivative of formula I ($R_9$=H). This product may be N-acylated at the aliphatic nitrogen by reaction with acetic anhydride in pyridine, with or without a co-solvent, to provide 2-acetyl derivatives of formula I wherein $R_9$=H.

In FIG. 2, a substituted tryptamine is cyclized by reaction with glyoxylic acid using acid catalysis to form a tricyclic carboxy product. This product may then be decarboxylated under acid catalysis to produce a tetrahydro-$\beta$-carboline derivative of formula I (wherein $R_9$=H). This product may then be N-acylated at the nitrogen of the aliphatic six membered ring (not shown) with acetic anhydride in pyridine, or without a co solvent.

Figure 3:
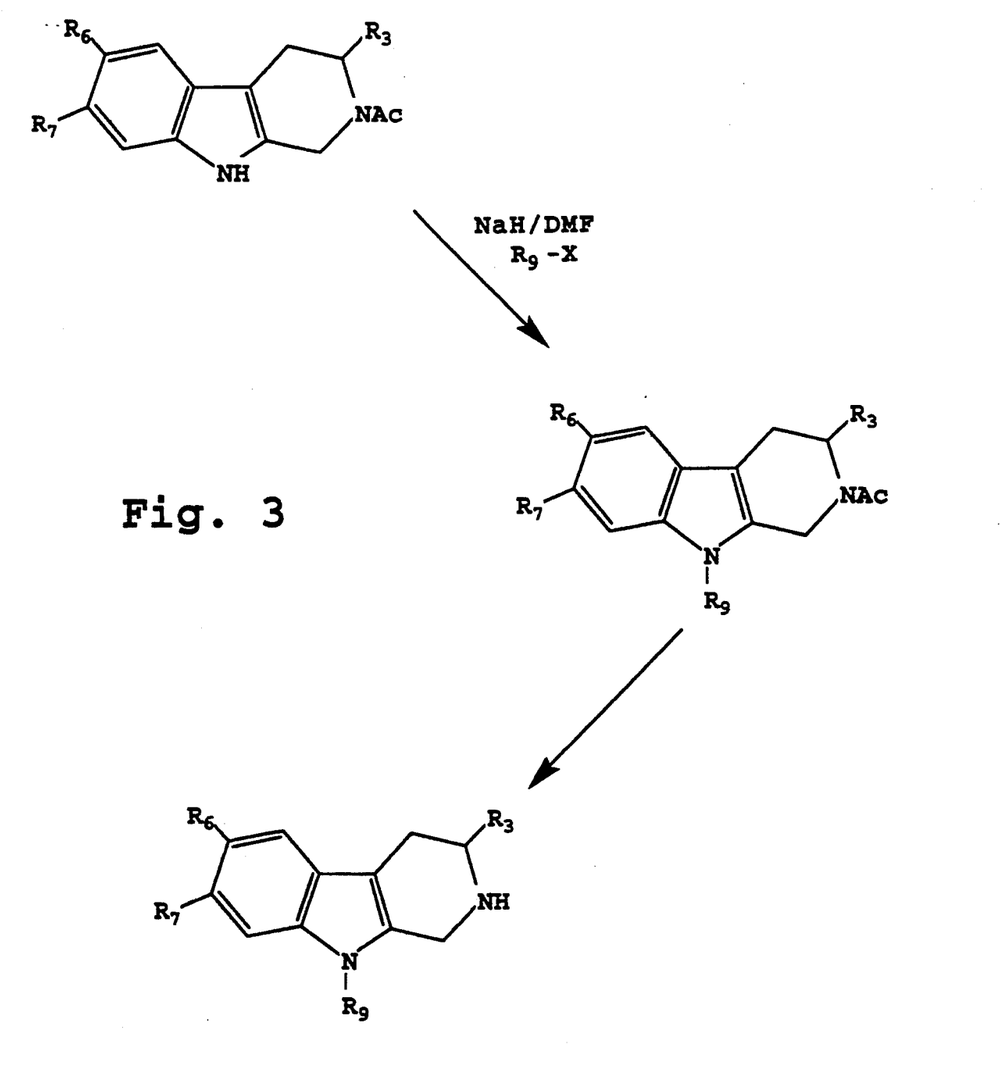
FIG. 3. shows a synthetic route to 1,2,3,4-tetrahydro-β-carbolines derivatized at the aromatic nitrogen.
Figure 4A:
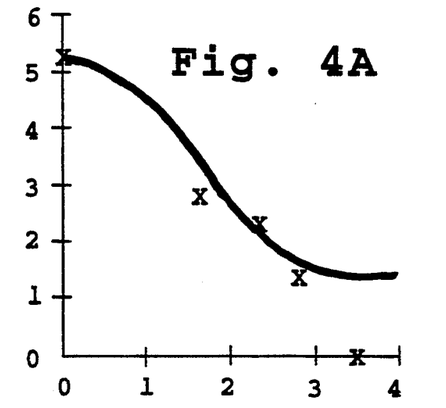
FIGS. 4A-4F show the dose-response Curves for THBC compounds 23,21,19,8,20 and 14, respectively.
Figure 4B:
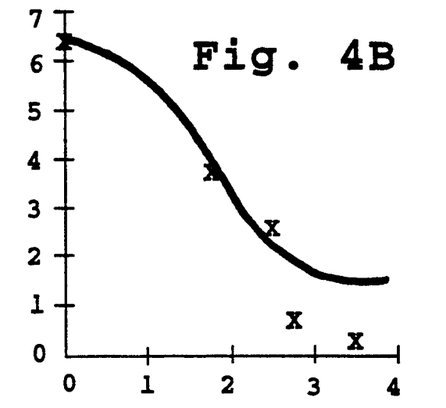
Figure 4C:
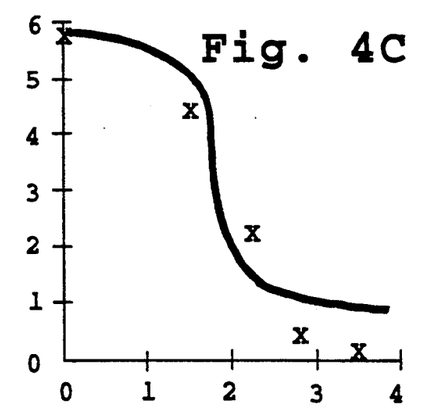
Figure 4D:
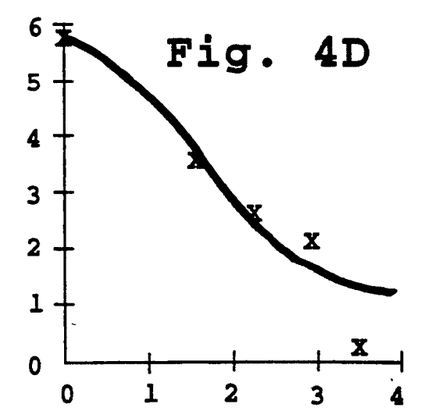
Figure 4E:
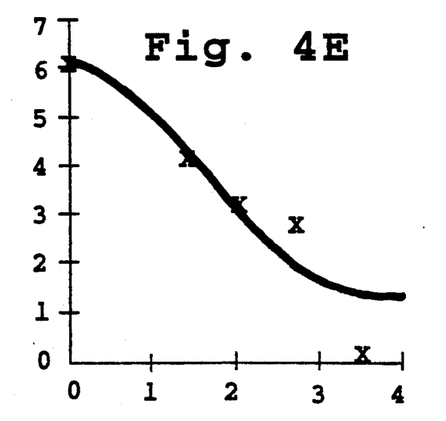
Figure 4F:
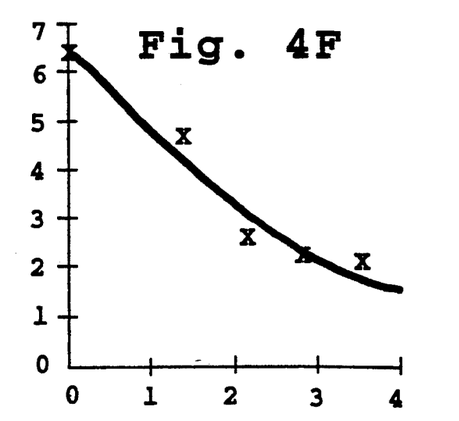

In FIG. 3 the N-acylated product just described is N-alkylated at the aromatic nitrogen by reacting the compound with an alkyl halide (e.g., ethyl bromide) in an anhydrous solvent, such as imethylformamide (DMF), and in the presence of sodium hydride (NaH). Deacylation of the compound may then be performed by standard procedures, such as refluxing under alkaline conditions.

It will be appreciated that a variety of substituted 1,2,3,4-tetrahydro-$\beta$-carbolines may be formed by the general methods just described. For example, those Compounds having substituents on the aromatic ring may be formed by purchasing suitably substituted tryptamines as starting materials (as is shown in Example 1 below for compounds 21, 8, 5, 10, 2 and 4). Alternatively, the aromatic ring may be derivatized using techniques for the addition of substituents to aromatic compounds which are well known in organic synthesis. For example, Fridel-Crafts alkylation may be used to place aliphatic substituents on the ring.

Similarly substituents at position 3 can be made using appropriately substituted tryptamines as starting materials, or using known methods of derivatizing aliphatic rings. For example, the compound $R_3$=COOH can be synthesized using tryptophan as the starting material (see compound 14 in Example 1 below). Compounds having substituents at the aromatic nitrogen ($R_9$) are easily synthesized using alkyl halides (see compounds 23, 21, 19, and 20 in Example 1).

Pharmaceutical compositions containing compounds of formula I, preferably as acid addition salts, may contain one or more pharmaceutical carriers. When the carrier serves as a diluent, it may be a solid, semisolid, or liquid material acting as a vehicle, excipient, or medium for the active ingredient. Pharmaceutical unit dosage forms may be prepared for administration by any of several routes including, but not limited to, oral and parenteral (especially by intramuscular and intravenous injection, or by subcutaneous implant or transdermal administration). Representative of such forms are tablets, soft and hard gelatin capsules, powders, lozenges, chewing gums, emulsions, suspensions, syrups, solutions, sterile injectable solutions, and sterile packaged powders. Compositions containing compounds of formula I may be formulated by procedures known in the art so as to provide rapid, sustained, or delayed release of any or all of the compounds after administration.

Solid pharmaceutical excipients such as magnesium stearate, calcium carbonate, silica, starch, sugar, talc, and the like may be used with other conventional pharmaceutical adjuvants including fillers, lubricants, wetting agents, preserving agents, disintegrating agents, flavoring agents, and binders such as gelatin, gum arabic, cellulose, methyl-cellulose, and the like, to form admixtures which may be used as such or may be tabulated, encapsulated, or prepared in other suitable forms as noted above. The preferred liquid diluent is physiologically normal saline. A general description of formulation is given in "Remington's Pharmaceutical Sciences."

Compounds of formula I produce significant, long-lasting reduction in feeding behavior when administered to mammals within 8 hours prior to meal presentation. Administration is preferably by oral dosage, but may be by transdermal application, intranasal spray, bronchial inhalation, suppository, parenteral injection (e.g., intramuscular or intravenous injection), and the like. At other doses, compounds of formula I are useful for suppressing obsessive-compulsive behavior, for altering macronutrient preferences, and for reducing craving of substances, particularly substances of abuse such as alcohol, tobacco, opiates and other narcotics.

The compound of formula I wherein $R_2=R_6=R_7=R_9=H$, and $R_3=COOH$ is particularly useful for partial appetite suppression. This compound provides partial suppression (where food intake is 20-70% of control) over a wide dose range, in contrast to full anorectic agents which provide large suppression (>80%) at effective dosages, and provide partial suppression over a very narrow range. As it is impractical to titrate the dosage of a full anorectic agent for each patient to achieve a particular partial appetite suppression, the method of the invention for partial appetite suppression is distinct and advantageous.

C. EXAMPLES

The examples presented below are provided as a further guide to the practitioner of ordinary skill in the art for preparing the THBC derivatives having the structures shown in Table 1 below.

TABLE 1

| (Reduction of Food Intake) | |
|---|---|
| Compound | Structure (substituent) |
| 1 | THBC (parent) |
|  | $R_{1,2,3,5,6,7,8} = H$ |
| 2 | $R_6 = OMe$ |
| 10 | $R_8 = Me$ |
| 16 | $R_2 = Ac$ |
| 5 | $R_7 = F$ |
| 4 | $R_6 = F$ |
| 27 | $R_2 = Ac, R_9 = Bz$ |
| 14 | $R_3 = COOH$ |
| 20 | $R_9 = Et$ |
| 8 | $R_6 = Cl$ |
| 19 | $R_9 = Bz$ |
| 21 | $R_9 = n\text{-}C_5H_{11}, R_6 = Me$ |
| 23 | $R_9 = n\text{-}C_5H_{11}$ |

EXAMPLE 1

Preparation of Compounds (23) 9-(n-pentyl)-1,2,3,4-tetrahydro-β-carboline hydrochloride was prepared as follows: Under a nitrogen atmosphere, 8.0 mmol of 2-acetyl-1,2,3,4-tetrahydro-β-carbolne (see 16 below) was dissolved in 40 mL dry dimethylformamide (DMF). The solution was stirred over ice, and NaH (2 g) was added under $N_2$. The suspension as stirred for 1 hour, and then 1-bromopentane (9.2 mmol, 1.14 mL, 1.39 g) was added slowly to the cooled suspension. After a further hours of stirring at ambient temperature, the mixture was filtered and the filtrate added to 320 mL 0.1 N HCl. Crude 2-acetyl-9-(n-pentyl)-1,2,3,4-tetrahydro-βcarboline separated as an oil. The oil was collected by centrifugation, washed with water, and dried over anhydrous $MgSO_4$.

A portion of the crude 2-acetyl-9-(n pentyl)1,2,3,4-tetrahydro-β-carboline (1.7 g) as heated at reflux for 4.5 hours in 2 N NaOH (50 mL) in methanol:water (2:3, v/v). The methanol was removed by evaporation under vacuum, and the crude 9-(n-pentyl)1,2,3,4-tetra-hydro-β-carboline free base was extracted into chloroform. This extract was dried over anhydrous $MgSO_4$, filtered, and the filtrate evaporated under vacuum. The hydrochloride salt was prepared by passing dry HCl through a solution of the crude free base in diethyl ether. The resulting precipitate was filtered and recrystallized from acetonitrile to yield pure 9-(n-pentyl)1,2,3,4-tetrahydro-β-carboline.

(21) 6-Methyl-9-(n-pentyl)-1,2,3,4-tetrahydro-β-carboline hydrochloride was prepared as follows: 5-Methyltryptamine hydrochloride (Sigma) was condensed with glyoxylic acid as described in part B above, and decarboxylated according to the procedure described in part C. The product, 6-methyl-1,2,3,4-tetrahydro-β-carboline hydrochloride was recrystallized from ethanol:water.

Under a nitrogen atmosphere, 7.7 mmol of the above-described 6-methyl compound (1.71 g) was dissolved in 4Q mL dry dimethylformamide (DMF). The solution was stirred over ice, and NaH (2 g) was added under $N_2$. The suspension was stirred for 1 hour, and then 1-bromopentane (9.2 mmol, 1.14 mL, 1.39 g) was added slowly to the cooled suspension. After a further 2 hours of stirring at ambient temperature, the mixture was filtered and the filtrate added to 320 mL 0.1 N HCl. Crude 6-methyl-9-(n-pentyl)-1,2,3,4-tetrahydro-β-carboline separated as an oil. The oil was collected by centrifugation, washed with water, and dried over anhydrous $MgSO_4$.

The hydrochloride salt was prepared by passing dry HCl through a solution of the crude free base in diethyl ether. The resulting precipitate was filtered and recrystallized from acetonitrile to yield pure 6-methyl-9-(n-pentyl)-1,2,3,4-tetrahydro-β-carboline.

(19) 9 benzyl-1,2,3,4-tetrahydro-β-carboline hydrochloride was prepared as follows: Under a nitrogen atmosphere, 8.0 mmol of 2-acetyl-1,2,3,4-tetrahydro- C β-carboline (see 16 below) was dissolved in 40 mL dry dimethylformamide (DMF). The solution was stirred over ice, and NaH 2 g) was added under $N_2$. The suspension was stirred for 1 hour, and then benzylbromide (9.2 mmol, 1.56 g) was added slowly to the cooled suspension. After a further 2 hours of stirring at ambient temperature, the mixture was filtered and the filtrate added to 320 mL 0.1 N HCl. Crude 2-acetyl-9-benzyl-1,2,3,4-tetrahydro-β-carboline separated as an oil. The oil was collected by centrifugation, washed with water, and dried over anhydrous $MgSO_4$.

A portion of the Orude -acetyl 9-benzyl-1,2,3,4-tetrahydro-β-carboline (1.7 g) was heated at reflux for 4.5 hours in 2 N NaOH (50 mL) in methanol:water 2:3, v/v). The methanol was removed by evaporation under vacuum, and the crude 9-benzyl-1,2,3,4-tetrahydro-β-carboline free base was extracted into chloroform. This extract was dried over anhydrous $MgSO_4$, filtered, and the filtrate evaporated under vacuum. The hydrochloride salt was prepared by passing dry HCl through a solution of the crude free base in diethyl ether. The resulting precipitate was filtered and recrystallized from acetonitrile to yield pure 9-benzyl-1,2,3,4-tetrahydro-β-carboline.

(8) 6-chloro-1,2,3,4-tetrahydro- -carboline hydrochloride was prepared as follows: 6-chlorotryptamine hydrochloride (Sigma) was condensed with glyoxylic acid as described in part B, and decarboxylated according to part C. The product, 6-chloro-1,2,3,4-tetrahydro-β-carboline hydrochloride was recrystallized from ethanol:water.

(20) 9-ethyl-1,2,3,4-tetrahydro-β-carboline hydrochloride was prepared as follows: Under a nitrogen atmosphere, 8.0 mmol of 2 acetyl-1,2,3,4-tetrahydro-β-carboline (see 16 below) was dissolved in 40 mL dry dimethylformamide (DMF). The solution was stirred over ice, and NaH (2 was added under $N_2$. The suspension was stirred for 1 hour, and then ethylbromide (9.2 mmol, 1.56 g) was added slowly to the Cooled suspension. After a further 2 hours of stirring at ambient temperature, the mixture was filtered and the filtrate added to 320 mL 0.1 N HCl. Crude 2-acetyl-9-ethyl-1,2,3,4-tetrahydro-β-carboline separated as an oil. The oil was collected by centrifugation, washed with water, and dried over anhydrous MgSO$_4$.

A portion of the crude 2-acetyl-9-ethyl-1,2,3,4-tetrahydro-β-carboline (1.7 was heated at reflux for 4.5 hours in 2 N NaOH (50 mL) in methanol:water (2:3, v/v). The methanol was removed by evaporation under vacuum, and the crude 9-ethyl-1,2,3,4-tetrahydro-β-carboline free base was extracted into chloroform. This extract was dried over anhydrous MgSO$_4$, filtered, and the filtrate evaporated under vacuum. The hydrochloride salt was prepared by passing dry HCl through a solution of the crude free base in diethyl ether. The resulting precipitate was filtered and recrystallized from acetonitrile to yield pure 9-ethyl-1,2,3,4-tetrahydro-β-carboline.

(14) (±) 3-carboxyl-1,2,3,4-tetrahydro-β-carboline was prepared as follows: (±) tryptophan benzyl ester hydrochloride (3.308 10 mmol, obtained from Bachem) was suspended in 0.05N H$_2$SO$_4$ (18.8 mL) with stirring, and 37% formaldehyde (0.938 mL) was added. The reaction mixture cleared, followed by crystallization of the product. Stirring continued for 24 hours before the product was filtered off and dried over P$_2$O$_5$. The crude material was recrystallized from ethanol/water and the crystals were dried over P$_2$O$_5$.

10 mmol of the product was next dissolved in 30 mL 2.5 N HCl and refluxed for one hour. Upon cooling the product precipitated from the reaction mixture, was isolated by filtration and dried under vacuum. The crystals were then dissolved in water, the pH was raised to 12 using 10 N NaOH, and the precipitated free base was centrifuged, washed with water, and dried under vacuum.

(27) 2 acetyl-9 benzyl-1,2,3,4-tetrahydro-β-carboline was prepared as follows: Under a nitrogen atmosphere, 8.0 mmol of 2 acetyl-1,2,3,4-tetrahydro-β-carboline (1.71 was dissolved in 4Q mL dry dimethylformamide (DMF). The solution was stirred over ice, and NaH (2 g) was added under N$_2$. The suspension was stirred for 1 hour, and then benzylbromide (9.2 mmol, 1.56 was slowly to the cooled suspension. After a further 2 hours of stirring at ambient temperature, the mixture was filtered and the filtrate added to 320 mL 0.1 N HCl. Crude 2-acetyl- 9-benzyl-1,2,3,4-tetrahydro-β-carboline separated as an oil. The oil was collected by centrifugation, washed with water, and dried over anhydrous MgSO:. The product was purified by standard chromatographic procedures using a 60:40 mixture of ether:-hexane.

(4) 6-fluoro-1,2,3,4 tetrahydro-β-carboline hydrochloride was prepared as follows: 6-fluorotryptamine hydrochloride (Sigma) was condensed with glyoxylic acid as described in part B, and decarboxylated according to part C. The product, 6-fluoro-1,2,3,4-tetrahydro-β-carboline hydrochloride was recrystallized from ethanol:water.

(5) 7-fluoro-1,2,3,4-tetrahydro-β-carboline hydrochloride was pre pare d as follows: 5-fluorotryptamine hydrochloride (Sigma) was condensed with glyoxylic acid as described in part B, and decarboxylated according to part C. The product, 5-fluoro-1,2,3,4-tetrahydro-β-carboline hydrochloride was recrystallized from ethanol:water.

(16) 2-acetyl-1,2,3,4-tetrahydro-β-carboline was prepared as follows: 1 g of 1,2,3,4-tetrahydro-β-carboline (Sigma) was dissolved in a minimum of ethyl acetate, and pyridine 3 mL) was added along with acetic anhydride (1.5 mL). After 30 minutes, the mixture was dried and the resulting 2-acetyl-1,2,3,4-tetrahydro-β-carboline was recrystallized from acetone.

(10) 8 methyl-1,2,3,4-tetrahydro-β-carboline was prepared as follows: 8-Methyltryptamine hydrochloride (Sigma) was condensed with glyoxylic acid as described in part B above, and decarboxylated according to the procedure described in part C. The product, 8-methyl-1,2,3,4-tetrahydro-β-carboline hydrochloride was recrystallized from ethanol:water.

(2) 6-methoxy 1,2,3,4-tetrahydro-β-carboline was prepared as follows: 5 hydroxytryptamine hydrochloride (Sigma) was condensed with glyoxylic acid as described in part B above, and decarboxylated according to the procedure described in part C. The product, 6-hydroxy-1,2,3,4-tetrahydro-β-carboline hydrochloride was dried over MgSO$_4$, dissolved in anhydrous and reacted with an equivalent of methyl iodide. The final product, 6-methoxy-1,2,3,4-tetrahydro-β-carboline, was recrystallized from ethanol:water.

EXAMPLE 2

Reduction of Food Intake

Dose ranging studies showed that compounds of formula I significantly reduced food intake when administered parenterally to rats in amounts appreciably lower than 25 mq/Kg.

Adult male rats weighing between 250 and 300 g were acclimated to laboratory conditions for a period of 4-5 days, during which they were allowed unrestricted access to food (Ralston-Purina #5001M) and water. All animals were housed in individual cages. The animal facility was maintained on a 12:12 hr light-dark schedule at 22° C.

Fasted animals were sorted into groups of 10-12 each by weight and baseline food intake. Each was then given saline containing 0-32 mg/Kg of a compound of the invention (or THBC) by intraperitoneal injection. After 20 minutes, animals were allowed access to food and water. Cumulative food intake was measured at 1 hour post-injection.

The measured food intake was plotted as a function of the natural logarithm of the drug concentration (ln(Dose)) given to the animal for each of the compounds listed above. A dose response curve of the functional form: Intake $= \alpha + (1-\alpha)/[1+\exp(\beta- \ln(Dose))]$ was fit to each of the data sets using the NONLIN feature of the Systat ™ statistical analysis software package for the Macintosh ™ (Systat, Evanston, Il). The data and the fitted curves for compounds 23, 21, 19, 8, 20 and 14 of the invention (as defined in Section B) are shown in FIGS. 4A-4F, respectively.

The dose level which caused a 50% reduction in food intake, hereinafter referred to as the IC$_{50}$ of the compound, was then determined by the formula IC$_{50}$=[(Intake-(t$_o$)−α)/(1−Intake(t$_o$))]$^{1/}$+β/, where the measured intake of food at time =0, and the coefficients α, β, and were obtained from the curve fitting procedure described above. The IC$_{50}$ values for THBC and thirteen other compounds, including those of the invention, were calculated and are shown in Table 2.

In the examples herein, compounds were administered parenterally. In clinical usage as an anorectic agent in mammals, particularly humans, the oral, intranasal, or transdermal routes of administration would be preferred. In the case of intraperitoneal administration in rodents, amounts as low as about 1.5 mg/Kg of body weight have been shown to achieve effective significant appetite suppression

TABLE 2

(Reduction of Food Intake)

| Compound | Structure | Activity LOG ($IC_{50}$) ($\mu$mole/kg) |
|---|---|---|
| 1 | THBC | −1.84 |
| 2 | $R_6$ = OMe | −1.79 |
| 10 | $R_8$ = Me | −1.79 |
| 16 | $R_2$ = Ac | −1.79 |
| 5 | $R_7$ = F | −1.67 |
| 4 | $R_6$ = F | −1.59 |
| 20 | $R_9$ = Et | −1.51 |
| 14 | $R_3$ = COOH | −1.48 |
| 27 | $R_2$ = Ac, $R_9$ = Bz | −1.47 |
| 8 | $R_6$ = Cl | −1.46 |
| 19 | $R_9$ = Bz | −1.35 |
| 23 | $R_9$ = n-$C_5H_{11}$ | −1.26 |
| 21 | $R_9$ = n-$C_5H_{11}$, $R_6$ = Me | −1.23 |

EXAMPLE 3

Partial Appetite Suppression

Compound 14 $R_2=R_6=R_7=R_9=H$, $R_3=$COOH) demonstrated qualitatively different dose-response characteristics from THBC. Unlike THBC, compound 14 will not depress feeding behavior over a comparatively large feeding range. This feature, termed "partial suppression" of feeding behavior, greatly increases the margin of safety, as overuse of the compound will not induce fatal anorexia.

Figure 5A:
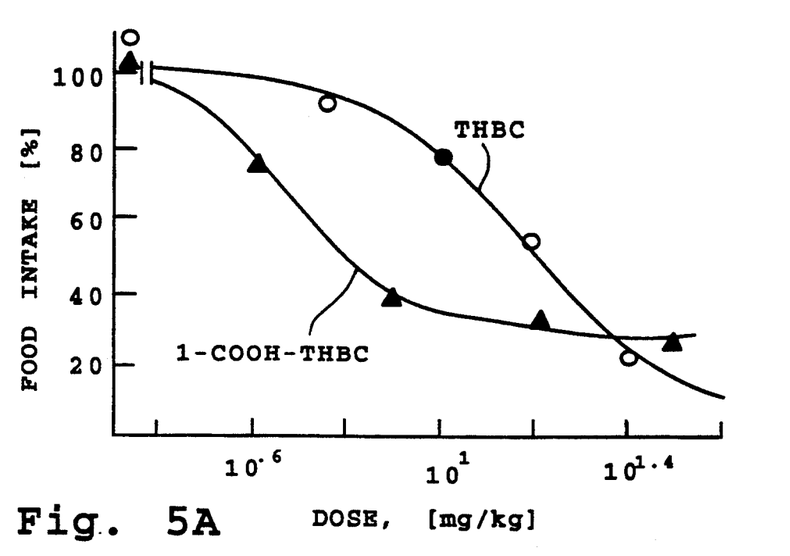
FIGS. 5A and 5B are plots of dose response for THBC and 3-carboxy-1,2,3,4 tetrahydro-βcarboline (5A) or 2-acetyl-1,2,3,4 tetrahydro-β-carboline (5B).
Figure 5B:
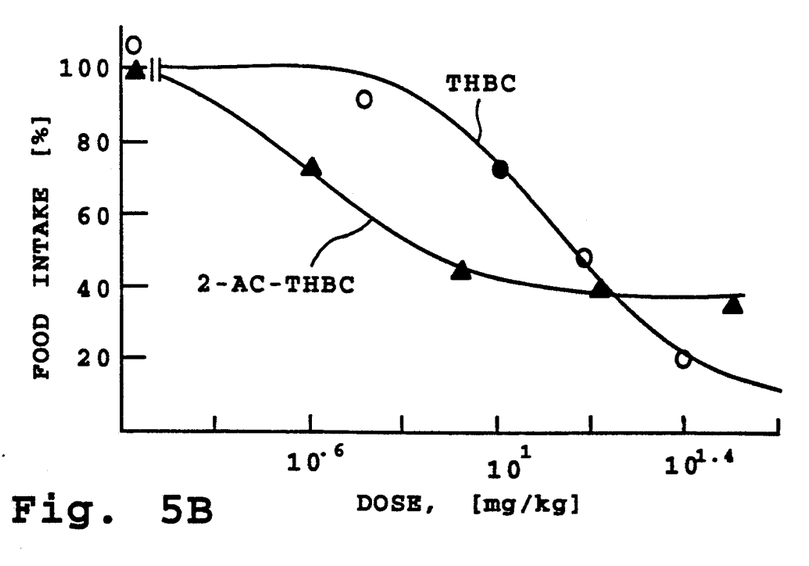

Reduction in food intake over one hour was measured against the dose per unit body weight for THBC and compound 14. The results are shown in FIG. 5A, which compares compound 14 with THBC.

The data demonstrate that THBC effected little feeding depression at low dosage, but relatively complete feeding depression at higher dosage, with a comparatively narrow range of concentration in the transition region. In contrast, compound 14 exhibited moderate feeding depression over a broad dosage range, beginning at dosages lower than those required for THBC, and extending past dosages at which THBC caused complete feeding cessation. The same behavior was observed for compound 16 ($R_2$=AC, $R_3=R_6=R_7=R_9=H$).

EXAMPLE 4

Alteration of Macronutrient Preference

This example demonstrates alteration of macronutrient preference in rats.

Sixty adult male rats (Sprague-Dawley, 225–300 g) were acclimated to laboratory conditions for a period of 10 days, during which they were allowed unrestricted access to food (Ralston Purina #5001M) and water. All subjects were housed in individual cages, and the animal facility was maintained on a 12:12 hour light:dark cycle at 24°–27° C.

The animals were assigned to six groups (ten per group), then allowed to consume, ad libitum, one of two iso-nitrogenous test diets containing either 75% or 25% carbohydrate. After three days, the food jars were removed. After an additional twenty-four hours, the rats were administered either a saline solution, or a compound of formula I (at a dose of 1.5 or 3.0 mg/Kg of body weight); then the rats were given immediate access to the test diets. The cumulative amount, in grams (mean ± SEM), of each diet consumed by the experimental and control groups during the subsequent twenty-four-hour period was recorded.

The results indicate that the animals receiving a compound of the invention consumed significant less of the high carbohydrate diet than the controls, but both groups consumed equivalent amounts of the low carbohydrate diet.

Thus, compounds of the invention selectively suppress carbohydrate cravings when administered at doses lower than the dosage effective for global reduction in appetite. This demonstrates the utility of the present invention as a method for reducing substance cravings per se, insofar as food cravings model clinical syndromes in which there is excessive preoccupation with, or urges for, specific habituating substances (Glassman et al., Science (1984) 226:864). Accordingly, this Example may be taken as evidencing efficacy in the treatment of alcohol, tobacco, or drug (particularly opiate) addiction.

EXAMPLE 5

Formulations (A) A representative capsule formulation is prepared as follows:

| Compound | 50.0 mg |
|---|---|
| starch | 3.0 mg |
| magnesium stearate | 3.0 mg |
| lactose | 110.0 mg |
| polyvinylpyrrolidone | 3.0 mg |

The compound of formula I, starch, magnesium stearate, lactose, and polyvinylpyrrolidone are granulated in methanol, dried, and loaded into capsules. Alternatively, the mixture may be tableted by standard methods.

(B) An oral suspension is prepared as follows:

| Compound | 50.0 mg |
|---|---|
| fumaric acid | 5.0 g |
| NaCl | 2.0 g |
| methyl paraben | 0.1 g |
| granulated sugar | 25.5 g |
| sorbitol (70% aq) | 12.9 g |
| Veegum K | 1.0 g |
| flavorings | 0.03 mL |
| colorings | 0.5 mg |
| distilled water | 100.0 mL |

The components are mixed together and stored in a sealed vessel.

(C) A formulation suitable for parenteral administration is prepared as follows:

| Compound | 40.0 mg |
|---|---|
| $KH_2PO_4$ buffer (0.4M) | 2.0 mL |
| adjust to pH = 7.0 with KOH (1N) | |
| add sterile, distilled water to a final volume of 20.0 mL | |

The components are mixed together and stored under sterile conditions.

D. QUANTITATIVE STRUCTURE ACTIVITY RELATIONSHIPS

The bioactivity of drug compounds can be quantitatively correlated with at least one, and typically two or more attributes of the drug molecule, such as the partitioning of the compound between hydrophilic and hydrophobic environments, expressed as its partition coefficient (P), the size or shape, often expressed in terms of molecular volume and surface area or steric parameters ($E_s$), the electronic nature of a system containing delocalized -electrons, and the overall effects of electronic distribution including the net atomic charge, dipole moment, and bond order or strength, and spatial relationships between key atoms in the molecule.

In particular, with respect to electronic parameters, the effect of chemical-group substitutions on Helectron systems have been well studied. Substituents generally will enlarge or distort these electron clouds; if the added group contains available electrons which occupy properly oriented orbitals, the delocalization will be extended; if the added species is either electron-withdrawing or electron-donating, the $\pi$cloud will be distorted. Molecular orbital (MO) theory provides calculational methods which quantitatively interpret the effects of such substitutions.

One such parameter, the Hammett parameter $\sigma$, is a measure of the electronic influence of chemical-group substituents on the reactivity of another group on the molecule; the two groups are isolated physically but communicate electronically through a delocalized $\pi$-electron system. Hammett $\sigma$ values are determined by measuring the effect of substituents on the dissociation of benzoic acid in water at 25° C. (March), and have been successfully applied to predictions for other aromatic ring systems. The effect of a substituent varies depending on its location; if it is located meta relative to the affected site, the value is reported as $\sigma_m$, or if it is para, $\sigma_p$. When a substitution is placed in the ortho (adjacent) position, intramolecular interactions introduce complications, these cases must be individually determined (Richardson).

Analogously, methods have been developed which allow quantification and prediction of many of the physical properties of molecules. For example, the partitioning of a chemical species between immiscible solvents is expressed mathematically as the partition coefficient (P), it is a measured classically (Hansch) by the determination of its distribution between octanol and water ($P_o$), the ratio is expressed in the log form. The effect on the partition coefficient can be predicted with reasonable accuracy from the properties of the atom or fragment which is added. Usually the partition coefficient of an added substituent is normalized by the coefficient of the unsubstituted ("parent") molecule and termed "$\pi$", LogP and $\pi$ can be determined either by direct measurement or calculation from tabulated factors by the fragment method (Hansch).

It will be appreciated that the contributions to the partition coefficient and electronic parameters of a drug molecule will be cumulative with respect to the chemical-group substitutions in the compound. For example, the addition of a given chemical-group substituent to an aromatic ring system will likely alter the partition coefficient of the compound, and if it is electron-donating or withdrawing, will alter the molecular orbital energies and charges on the atoms in a conjugated electron system. Any corresponding changes in bioactivity may be occurring as a consequence of either the modification in an isolated parameter or the synergism of more than one.

The method of quantitative structure-activity relationship (QSAR) analysis (Hansch), has shown that frequently there is a correlation between a selected bioactivity of a compound and parameters characterizing the solubility and electronic properties of the substituents, and that this can be expressed in a relatively simple mathematical formula of the general type:

$$-\text{Log(Activity)} = a\text{Log}(P)^2 + b\text{Log}(P) + c\sigma + d \quad (1)$$

where P and $\sigma$ are only shown as model parameters, which may alternatively, or additionally include such parameters as steric factors or molecular orbital energies. By determining the parameter values for each of the members of a group of active compounds, the coefficients (e.g., a, b, c and d) of the QSAR equation can be found by multivariate linear regression to a least squares fit of the parameters with the trend of the measured activities. Activity is typically defined as the concentration of Compound required to achieve a defined effect, for example, the concentration of a drug which produces 50% inhibition or a 90% inhibition of a measurable biological effect.

In the present analysis, changes observed in the appetite-suppressing activity of 20 substituted $\beta$-carbolines were analyzed for correlation with changes in structure introduced by substitutions at one or two positions on the molecule. The parameters which produced the best relationship for the compounds which were analyzed are listed in the accompanying table (Table 4). The physical parameters tested for correlation were $\pi$, which reflects the hydrophobicity of the added moiety, molecular volume and area, and molar refractivity (MR) which varies as a function of the size and shape of a molecule. Tabulated values were used when available HansCh or values for $\pi$ were calculated by the fragment method. The electronic parameter o did not show a clear relation when analyzed with a reference to the position about the ring, but its inclusion did improve correlation over a simple consideration of hydrophobicity and size.

Molecular orbital parameters, including net charge, energy, bond order of the molecule, and electron density, at each atom, and highest occupied molecular orbital (HOMO) and lowest unoccupied molecular orbital (LUMO) were calculated using an extended Huckel theory (EHT) calculation. An EHT program was obtained from the Quantum Chemical Program Exchange of Indiana University (QCPE), and modified for Macintosh II microcomputer.

Multiple linear regression was carried out by a computer program designed to test each possible set of four or fewer parameters. The maximum of four parameters was dictated by the statistical requirement in QSAR analysis for at least about 5 compound activity values per predictive parameter. The regression analysis was carried out with twenty compounds, fourteen which had greater molar activity than THBC, and five with lower molar activity. These values for activity, expressed as the $IC_{50}$ (dose sufficient to lower the food consumption to 50% of that of the control animals) are shown in Table 3. The regression equations which were generated were then sorted on the basis of (a) highest multiple R (a measure of degree to which the measured activity is accounted for by the equation) and (b) correlation between parameters (the degree to which parameters in the equations are independent). Specifically, equations which gave highest multiple squared R values, and showed a correlation between parameters of less than 20% were selected.

The following equation (2) equation gave the best fit to the activity data:

$$\log(1/IC_{50})32 \\ -0.0491\pi^2 + 0.416\pi + 0.118(qC_9\%)^* - 0.041(S'C_8-R)^{**} - 2.139$$

(n=20, multiple R=0.846, squared multiple r=0.715, adjusted squared multiple R =.639, residual =0.345 and F-ratio =9.42). L6 *Net Charge -nitrogen atom at $R_9$ L6 **Radical Superdelocalizability -carbon atom $C_8$ The statistical value which can be used to estimate the influence of the combination of the three selected parameters on the observed activity is squared multiple R. With the data in this set, about 72% of the variation in anti appetite activity is predicted.

Figure 6:
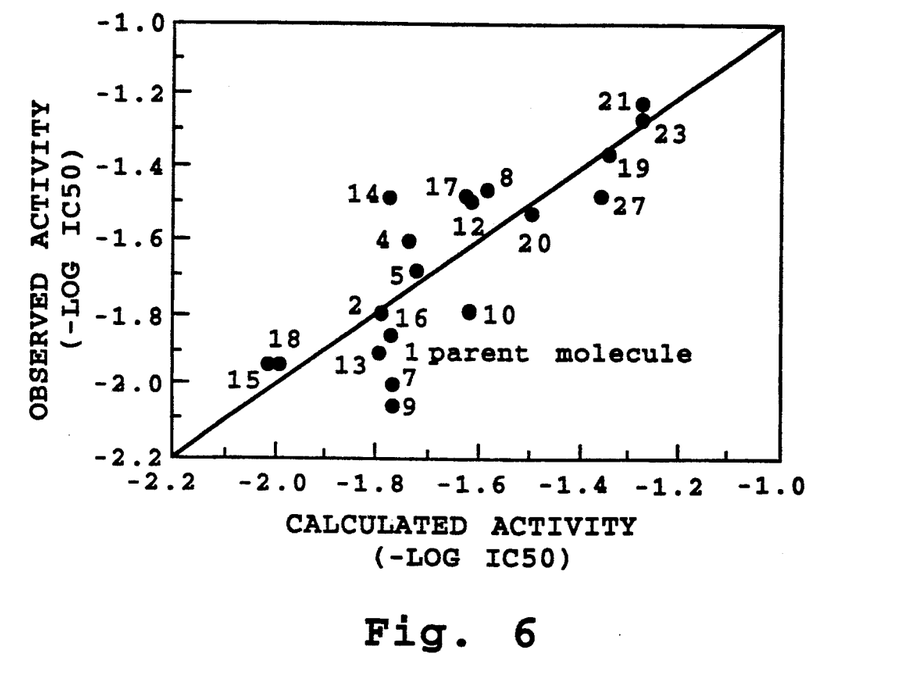
FIG. 6 shows the measured activity of the 19 derivatives and THBC (1), and a plot of the structure-activity relationship calculated from the compounds.

Using the values of the parameters given in Table 4, equation 2 was used to determine a calculated activity for each of the twenty test compounds. The results are shown in Table 3 and plotted in FIG. 6. The unit line in FIG. 6 represents exact correspondence between actual and predicted activities. As seen, the regression analysis produces a reliable correspondence between actual and predicted activity.

Also as seen from Table 3, the most active compounds, i.e., compounds more active than THBC, have predicted values between about −1 2 and −1.7 Thus, in accordance with one aspect of the invention, the $R_1$-$R_9$ substituents are so selected that the quantity:

$$-0.0491\pi^2 + 0.416\pi + 0.118(qC_9\%) - 0.041(S'C_8R) - 2.139$$

has a value between about −1.2 and 1.7, and preferably between about −1.2 and −1.5.

TABLE 3

AGREEMENT BETWEEN OBSERVED AND CALCULATED VALUES

| | | Log (1/IC$_{50}$): μmole/Kg | |
|---|---|---|---|
| Compound | Structure | Measured | Predicted |
| 21 | $R_6$ = Me, $R_9$ = Pentyl | −1.23 | −1.266 |
| 23 | $R_9$ = Pentyl | −1.26 | −1.267 |
| 19 | $R_9$ = Benzyl | −1.35 | −1.340 |
| 8 | $R_6$ = Cl | −1.46 | −1.585 |
| 27 | $R_9$ = Benzy, $R_2$ = Acetyl | −1.47 | −1.364 |
| 14 | $R_3$ = COOH | −1.48 | −1.773 |
| 17 | $R_5$ = Me | −1.48 | −1.620 |
| 12 | $R_6$ = Me | −1.49 | −1.607 |
| 20 | $R_9$ = Et | −1.51 | −1.477 |
| 4 | $R_6$ = F | −1.59 | −1.742 |
| 5 | $R_7$ = F | −1.67 | −1.731 |
| 10 | $R_8$ = Me | −1.79 | −1.616 |
| 16 | $R_2$ = Acetyl | −1.79 | −1.779 |
| 2 | $R_6$ = Methox | −1.79 | −1.777 |
| 1 | parent molecule $R_{1,2,3,5,6,7,8}$ = H | −1.84 | −1.773 |
| 13 | $R_3$ = Et | −1.89 | −1.788 |
| 15 | $R_3$ = COOH, $R_6$ = OH | −1.96 | −2.005 |
| 18 | $R_9$ = Formyl | −1.96 | −1.985 |
| 7 | $R_1$ = Me | −2.00 | −1.774 |
| 9 | $R_6$ = Me | −2.04 | −1.774 |

TABLE 4

STRUCTURAL PARAMETERS USED FOR QSAR ANALYSIS

| | | Hydrophobicity | | Electronic of of indole substituent | |
|---|---|---|---|---|---|
| Number | Substituent | Π | (Π)$^2$ | q(C$_9$) % | S'C$_8$R |
| 21 | $R_6$ = Me, $R_9$ = Pent | 3.67 | 13.47 | −0.17 | −0.64 |
| 23 | $R_9$ = Pent | 3.67 | 13.47 | −0.17 | −0.61 |
| 19 | $R_9$ = Benzy | 3.01 | 9.06 | −0.17 | −0.26 |
| 8 | $R_6$ = Cl | 1.71 | 2.92 | −0.18 | −0.16 |
| 27 | $R_9$ = Benzy, $R_2$ = Acetyl | 2.93 | 8.76 | −0.17 | −0.14 |
| 14 | $R_3$ = COOH | 1.00 | 1.00 | −0.49 | −0.53 |
| 17 | $R_5$ = Me | 1.56 | 2.43 | −0.49 | −0.28 |
| 12 | $R_6$ = Me | 1.56 | 2.43 | −0.22 | −0.61 |
| 20 | $R_9$ = Et | 2.02 | 4.08 | −0.46 | −0.71 |
| 4 | $R_6$ = F | 1.14 | 1.30 | −0.14 | −0.22 |
| 5 | $R_7$ = F | 1.14 | 1.30 | −0.09 | −0.48 |
| 10 | $R_8$ = Me | 1.56 | 2.43 | −0.49 | −0.38 |
| 16 | $R_2$ = Acet | 1.00 | 1.00 | −0.48 | −0.38 |
| 2 | $R_6$ = Methox | 0.98 | 0.96 | −0.39 | −0.57 |
| 1 | parent $R_{1,2,3,5,6,7,8}$ = H | 1.00 | 1.00 | −0.49 | −0.52 |
| 13 | $R_3$ = Et | 1.00 | 1.00 | −0.50 | −0.16 |
| 15 | $R_3$ = COOH, $R_6$ = OH | 0.33 | 0.11 | −0.51 | −0.59 |
| 18 | $R_9$ = Form | 0.35 | 0.12 | −0.23 | −0.39 |
| 7 | $R_1$ = Me | 1.00 | 1.00 | −0.49 | −0.51 |
| 9 | $R_6$ = Me | 1.00 | 1.00 | −0.49 | 0.49 |

The coefficients for the parameters for $\pi$ and $\pi^2$ indicate the importance of hydrophobicity to compound activity. The negative sign of the $\pi^2$ term indicates that a substitution which adds a $\pi$ of greater than about 4.6 (all other parameters remaining unaffected) would reverse the trend, or be too lipophilic. The size of the coefficient (0.416) and the relative magnitudes of the values for $\pi$ indicate that substituents that optimize hydrophobicity would contribute predominantly to the design of preferred molecular structures.

The electronic effect of substitutions at positions in the indole ring are also seen to be important. The ideal substituent would increase the net charge (a negative value for the indole nitrogen) in a positive direction. One way to achieve this is to substitute an aliphatic group at an aliphatic group. As can be seen in Table 4, the value for the unsubstituted nitrogen is 0.49, and for aliphatic substitutions, about −0.2. The size of the substituent is not critical to net charge, so a group large enough to optimize the parameter is preferred.

A radical superdelocalizability at the $C_8$ position should also be considered in the selection of ring substituents. The superdelocalizability term may suggest a site at which a reaction can occur, or one at which polarizability optimizes an interaction, such as hydrogen-bond formation.

The results of the QSAR study indicate how the substituents $R_2$-$R_9$ may be selected to produce active THBC analogs, in accordance with the invention. As an example, the compound in a butyl group is placed with one end attached at R9 and its opposing end at R1, forming a fourth ring (structure A in FIG. 7) is considered. The calculated value of $\pi$ for the group is 2.76, and extended Hückel calculations estimate a value of −0.241 for the charge at the substituted nitrogen. The value calculated for Log(1/activity) of −1.44 is comparable to that of tested compounds 23 and 19.

Figure 7A:
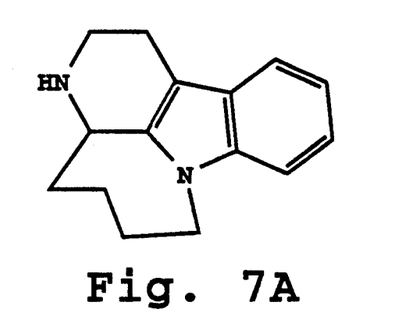
FIG. 7 shows three THBC derivatives (A,B, and C), which are predicted from structure values, to have high (A and C) and low (B) activity.
Figure 7B:
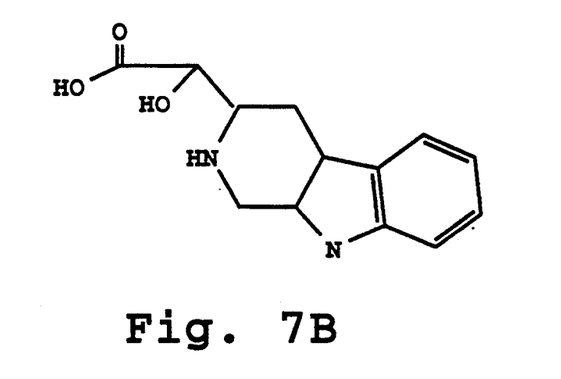
Figure 7C:
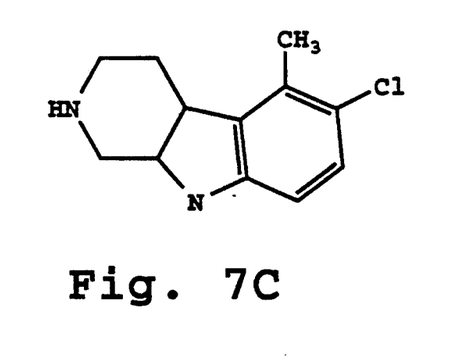

By contrast, compound B in FIG. 7 is predicted by the analysis to have low activity. The compound has a polar substituent (calculated $\pi$ value is −0.66) at $R_3$, and the indole nitrogen is unsubstituted, with a net charge of -0.521 for the indole nitrogen. From equation 2, the calculated activity for B would be obtained from: $-0.049(-0.49)^2 + 0.42(-0.49) + 0.12(0.521) - 0.041 (-0.26) - 2.139 = -2.26$. This value is outside of the desired range of $-1.2$ and $-1.7$ and thus the compound would not be expected to have high activity relative to THBC.

Another example of a type of structural modification of the basic THBC structure is shown in FIG. 7, compound C. In this molecule, the indole nitrogen is not substituted, but two groups are added to the indole ring, in position $R_5$ a methyl and in $R_6$, chloro. This results in a combined increase in $\pi$ of 3.27, while the value of the charge on the indole nitrogen remains almost the same as the parent, at $-0.533$. The substitution of these values into the equation (2) leads to a calculated $-\log$ activity of $-1.36$, or close to that of compounds 27 and 19.

More generally, the $R_2$–$R_9$ substituents are selected, in accordance with the invention such that the expression:
$-0.0491\pi^2 + 0.416\pi + 0.118(qC_9\%)^* - 0.041(S'C_8R)^{**} -2.139$ is less than about $-1.77$.

The foregoing is offered primarily for purposes of illustration. It will be readily apparent to those skilled in the art that numerous variations, modifications and substitutions, in the materials and methods described herein may be made without departing from the scope of the invention.

It is claimed:

1. A composition for suppressing appetite in a mammal, which comprises:
   a pharmaceutically acceptable excipient, and an effective appetite suppressive amount of a compound selected from the group consisting of:
   6fluoro-9-(n-pentyl)-1,2,3,4-tetrahydro-β-carbolien,
   6-chloro-9-(n-pentyl)-1,2,3,4-tetrahydro-β-carbolien, and
   2-acetyl-9-benzyl-1,2,3,4-tetrahydro-β-carbolien.

2. A method for suppressing appetite in a mammal, which comprises:
   administering to the mammal in need thereof a pharmaceutically acceptable excipient, and an effective appetite suppressive amount of a compound selected from the group consisting of:
   6-methoxy-9-(n-pentyl)-1,2,3,4-tetrahydro-β-carbolien,
   6-fluoro-9-(n-pentyl)-1,2,3,4-tetrahydro-β-carboline, and
   2-acetyl-9-benzyl-1,2,3,4-tetrahydro-β-carboline

* * * * *